United States Patent [19]

McGhee

[11] Patent Number: 5,977,008
[45] Date of Patent: Nov. 2, 1999

[54] SELECTIVE INTRODUCTION OF ACTIVE SITES FOR HYDROXYLATION OF BENZENE

[75] Inventor: William D. McGhee, St. Louis, Mo.

[73] Assignee: Solutia Inc., St. Louis, Mo.

[21] Appl. No.: 09/078,454

[22] Filed: May 13, 1998

Related U.S. Application Data

[62] Division of application No. 08/700,146, Aug. 20, 1996, Pat. No. 5,808,167.

[51] Int. Cl.$^6$ .................................................. B01J 29/072
[52] U.S. Cl. .............................. 502/62; 502/60; 502/74; 502/85
[58] Field of Search ................................ 502/60, 62, 74, 502/85

[56] References Cited

U.S. PATENT DOCUMENTS

| | | |
|---|---|---|
| 3,945,943 | 3/1976 | Ward . |
| 4,258,222 | 3/1981 | Möhring et al. ........................ 568/863 |
| 4,982,013 | 1/1991 | Gubelmann et al. ................... 568/771 |
| 5,001,280 | 3/1991 | Gubelmann et al. ................... 568/716 |
| 5,019,657 | 5/1991 | Gubelmann et al. ................... 568/774 |
| 5,055,623 | 10/1991 | Gubelmann et al. . |
| 5,110,995 | 5/1992 | Kharitonov et al. .................... 568/800 |
| 5,171,553 | 12/1992 | Li et al. .................................. 423/239 |
| 5,502,259 | 3/1996 | Zakoshansky et al. ................. 568/754 |
| 5,520,895 | 5/1996 | Sharma et al. ........................ 423/239.1 |

FOREIGN PATENT DOCUMENTS

| | | |
|---|---|---|
| 0 406 050 A2 | 6/1990 | European Pat. Off. . |
| 5-16179 | 2/1993 | Japan . |
| 2 010 790 | 4/1994 | Russian Federation . |
| 2 116 974 | 3/1993 | United Kingdom . |
| WO 95/27560 | 10/1995 | WIPO . |
| WO 95/27691 | 10/1995 | WIPO . |
| WO 9527560 | 10/1995 | WIPO . |

OTHER PUBLICATIONS

Li et al. (1992) Catalytic Decomposition Of Nitrous Oxide On Metal Exchanged Zeolites Applied Catalysis B: Environmental 1, L21–29; Elsevier Science Publishers B.V., Amsterdam.

Sobolev et al. (1993) Catalytic Properties Of ZSM–5 Zeolites In $N_2O$ Decomposition: The Role Of Iron; Journal of Catalysis 139, 435–443; Academic Press, Inc.

Sobolev et al. (1993) Stoichiometric Reaction Of Benzene With α–Form Of Oxygen On Fezsm–5 Zeolites. Mechanism Of Aromatics Hydroxylation By $N_2O$; Journal of Molecular Catalysis 84, 117–124; Elsevier Science Publishers B.V., Amsterdam.

Panov et al. (1992) Oxidation Of Benzene To Phenol By Nitrous Oxide Over Fe–ZSM–5 Zeolites; Applied Catalysis A: General 82, 31–36, Elsevier Science Publishers B.V., Amsterdam.

Kharitonov et al. (1993) Ferrisilicate Analogs Of ZSM–5 Zeolite As Catalysts For One Step Oxidation Of Benzene To Phenol; Applied Catalysis A: General 98, 33–43, Elsevier Science Publishers B.V., Amsterdam.

Burch et al. (1993) Factors Affecting The Deactivation Of Various Zeolites Used As Catalysts For The Direct Partial Oxidation Of Benzene To Phenol Applied Catalysis A: General 106, 167–183, Elsevier Science Publishers B.V., Amsterdam.

Burch et al. (1993) Investigation Of Zeolite Catalysts For The Direct Partial Oxidation Of Benzene To Phenol; Applied Catalysis A: General 103, 135–162, Elsevier Science Publishers B.V., Amsterdam.

Burch et al. (1993) Direct Partial Oxidation Of Benzene To Phenol On Zeolite Catalysts Applied Catalysis A: General 86, 139–146, Elsevier Science Publishers B.V., Amsterdam.

Panov et al. (1993) Oxidative Hydroxylation Using Dinitrogen Monoxide; A Possible Route For Organic Synthesis Over Zeolites, Applied Catalysis A: General, 98, 1–20, Elsevier Science Publishers B.V., Amsterdam.

Vereshchagin et al, Conversion Of Ethane On Zeolite Catalysts In The Presence Of Oxygen And Nitrogen(l) Ox De, Izv. Akad. Nauk SSSR, (1988), 1718–1722 (English abstract translated from Russian article).

Dvorak et al. (1970) Determination Of The Specific Copper Surface Area By Chromatographic Technique, Journal of Catalysis 18, 108–114, Academic Press, Inc.

Evans et al. (1983) On The Determination Of Copper Surface Area By Reaction With Nitrous Oxide; Applied Catalysis 7, 75–83, Elsevier Science Publishers B.V.

Iwamoto et al. (1983) Catalytic Oxidation By Oxide Radical Ions. 1. One–Step Hydroxylation Of Benzene To Phenol Over Group 5 And 6 Oxides Supported On Silica Gel; The Journal of Physical Chemistry 87, No. 6, The American Chemical Society.

Ono et al. (1988) Functionalization Of Benzene By Its Reaction With Nitrogen Oxides Over Solid–Acid Catalysts, Heterogeneous Catalysis and Fine Chemicals, pp. 75–82, Elsevier Science Publishers B.V., Amsterdam.

Suzuki et al. (1988) Hydroxylation Of Benzene With Dinitrogen Monoxide Over H–ZSM–5 Zeolite, Chemistry Letters, pp. 953–956, The Chemical Society of Japan.

Panov et al. (1990) The Role Of Iron In $N_2O$ Decomposition On ZSM–5 Zeolite And Reactivity Of The Surface Oxygen Formed, Journal of Molecular Catalysis 61, 85–97, Elsevier Sequoia.

Sobolev et al. (1991) Anomalously Low Bond Energy Of Surface Oxygen On FeZSM–5 Zeolite, Mendeleev Communications, No. 1, pp. 29–30.

Zholobenko (1993) Preparation Of Phenol Over Dehydroxylated HZSM–5 Zeolites Mendeleev Communications, pp. 23–24.

(List continued on next page.)

*Primary Examiner*—Thomas Dunn
*Attorney, Agent, or Firm*—Arnold, White & Durkee

[57] ABSTRACT

A zeolite catalyst, which can be used in a process for hydroxylating benzene to phenol, is treated with an aqueous solution containing ferric or ferrous ions, and is treated with an aqueous solution containing dithionate ions. The treated catalyst exhibits improved selectivity and stability in the benzene hydroxylation process.

9 Claims, 4 Drawing Sheets

OTHER PUBLICATIONS

Hafele etal. (1996) Hydroxylation of Benzene on ZSM5 Type Catalysts, DGMK Conference, Catalysis On Solid Acids And Bases, pp. 243–251.
Derwent abstract; JP 5 009 142 (1993).
Derwent abstract, JP 4 334 333 (1992).
Derwent abstract, JP 4 021 645 (1992).
Derwent abstract, JP 6 009 464 (1994).
Derwent abstract, JP 6 040 976 (1994).
Derwent abstract, EP 406 050 (1990).

SELECTIVE INTRODUCTION OF ACTIVE SITES FOR HYDROXYLATION OF BENZENE

This is a division of application Ser. No. 08/700,146 filed Aug. 20, 1996, now U.S. Pat. No. 5,808,167.

BACKGROUND OF THE INVENTION

The present invention relates to improved catalysts for use in the hydroxylation of benzene or derivatives thereof to form phenol or related compounds.

Phenol or a derivative thereof can be produced by a single-step oxidative hydroxylation of benzene or a derivative thereof, using nitrous oxide over a zeolite catalyst. For example, PCT publication WO 95/27560 describes such a process that employs a zeolite catalyst whose performance is enhanced by hydrothermal treatment. The zeolite catalyst is treated with a water vapor-containing gas phase at a temperature in the range of 350 to 950° C.

A need exists for catalysts having improved performance, so that the conversion of an aromatic hydrocarbon such as benzene to phenol or another desired product can be made more economical. One potential way of improving catalyst performance is by selective introduction of sites for hydroxylation, for example by introducing iron into the catalyst. Introduction of iron into zeolites can be done either during the crystallization (synthesis) of the zeolite or by some post-synthesis technique. Introduction of active iron via synthesis can present complications due to longer crystallization times and introduction of iron into sites which are not responsible for productive pathways. Therefore, post-synthesis introduction of iron is potentially attractive because it avoids the need to develop new crystallization techniques. However, post-synthesis methods have not been entirely satisfactory so far, in part because not all post-synthesis methods permit selective introduction of iron.

SUMMARY OF THE INVENTION

The present invention relates to a method of preparing a catalyst for oxidation of an aromatic compound, such as benzene or a derivative thereof. The method comprises the steps of treating a zeolite catalyst with an aqueous solution containing ferric or ferrous ions, and treating the catalyst with an aqueous solution containing dithionate ions. These steps are performed after the catalyst is synthesized. The amount of ferric or ferrous ions present in the first solution is effective to introduce iron into the catalyst that will be effective to catalyze the hydroxylation reaction. The amount of dithionate ions in the second solution is effective to remove iron from the catalyst that would catalyze the formation of undesired byproducts.

The method can optionally include the further step of hydrothermally treating the catalyst. Such hydrothermal treatment of the catalyst preferably comprises exposing the catalyst to a gas comprising 1–100 mole percent water at a temperature between approximately 350–950° C.

In a particular embodiment of the invention, the catalyst is further treated with an acid.

The sequence of these steps can be varied. For example, in one embodiment, the catalyst is first hydrothermally treated, then is treated with the solution of ferric or ferrous ions, and subsequently is treated with the solution of dithionate ions. In another embodiment, the catalyst is first treated with the solution of ferric or ferrous ions, is subsequently hydrothermally treated, and subsequent to that step is treated with the solution of dithionate ions. The acid treatment can be done before, after, or inbetween the ferric/ferrous and dithionate treatments. Whatever the sequence, the catalyst is preferably calcined after the treatment with ferric or ferrous ions and before the next step.

Another particular embodiment of the present invention is a method of preparing a catalyst for oxidation of benzene or a derivative thereof, which comprises the steps of (a) hydrothermally treating a zeolite catalyst by exposing the catalyst to a gas comprising 1–100 mole percent water at a temperature between approximately 350–950° C., (b) treating the catalyst with an aqueous solution containing ferric or ferrous ions, (c) calcining the catalyst, (d) treating the catalyst with an aqueous solution containing dithionate ions, (e) treating the catalyst with an acid and (f) calcining the catalyst.

Another aspect of the present invention relates to a modified zeolite catalyst prepared by the methods described above. Yet another aspect of the invention relates to a method for hydroxylating an aromatic compound, comprising contacting an aromatic compound with a modified zeolite catalyst, the catalyst having been prepared by a method as described above.

In one embodiment, the present invention involves the following general reaction.

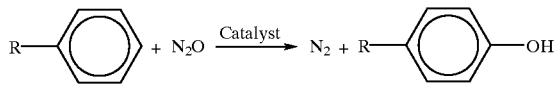

R can be a wide variety of substituents, including for example hydrogen, halogen, alkyl groups having from 1–4 carbon atoms, or a hydroxyl group. The aromatic starting material can optionally have other substituents in addition to the R group.

Using the present invention, introduction of active sites in a zeolite catalyst for the hydroxylation of benzene or other aromatic substrates can be accomplished in a selective manner, which increases the activity of the catalyst without increasing side reactions such as coke formation or over-oxidation to carbon dioxide and carbon monoxide. This is because the dithionate treatment selectively removes unwanted iron species without removing iron that is involved in the hydroxylation chemistry. This selective removal is surprising as the literature indicates that reductive treatment with dithionate removes iron oxides from the zeolite.

Further, the post-synthesis nature of the iron addition in the present invention avoids the problems associated with iron introduction during zeolite synthesis, and makes the process more versatile than prior art processes.

DESCRIPTION OF SPECIFIC EMBODIMENTS

Figure 1:
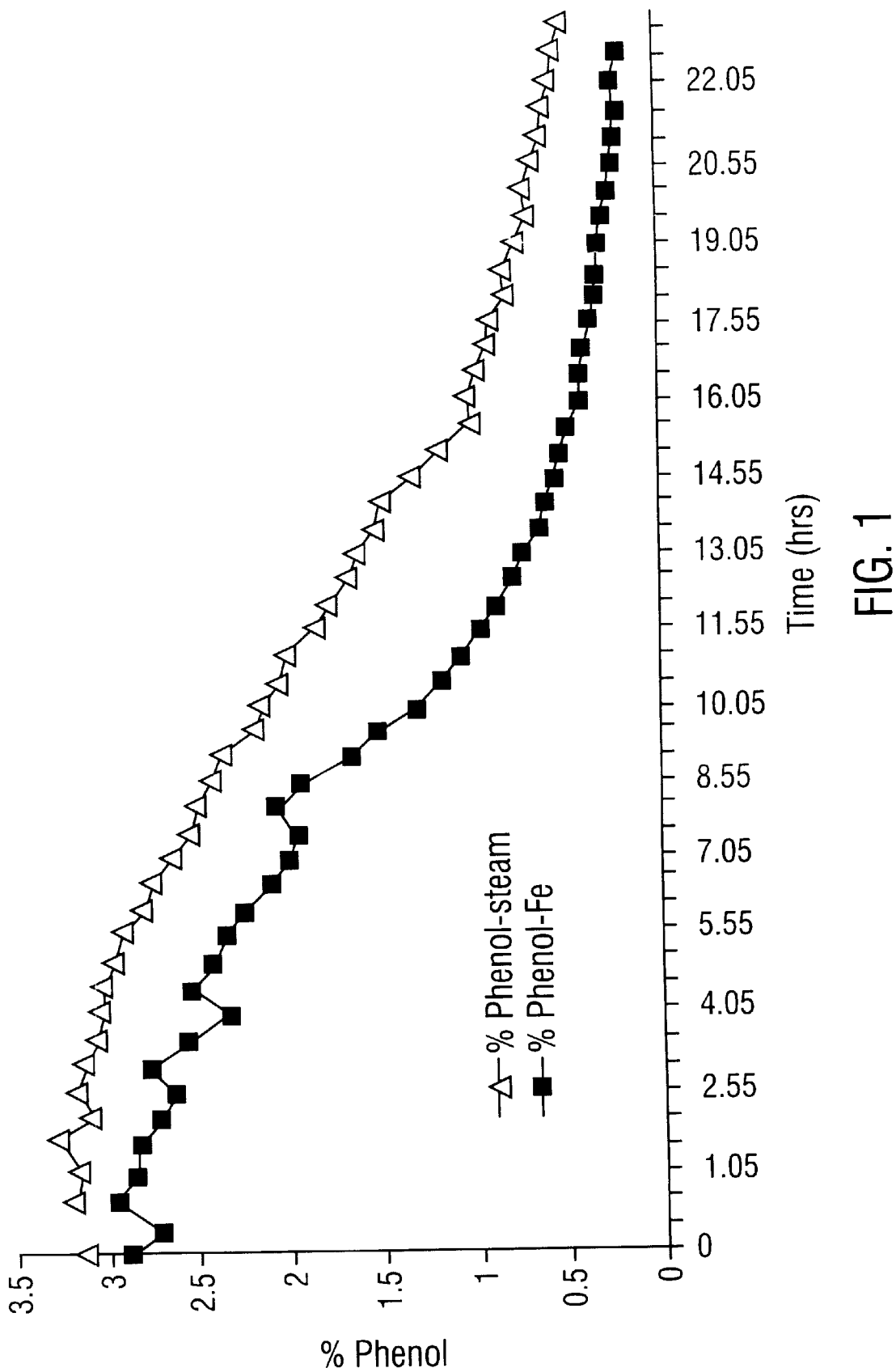
FIG. 1 is a graph of the change over time in the percentage of phenol in the product stream of a benzene hydroxylation process using catalyst in which (a) the catalyst had been hydrothermally treated ("Phenol-steam"), or (b) the catalyst had been hydrothermally treated and then had iron added by treatment with ferric ammonium oxalate ("Phenol-Fe").

Aromatic compounds can be hydroxylated using the catalyst of the present invention. Preferred aromatic compounds have from about 6–18 carbon atoms. The compounds can be substituted with one or more substituents such as halogens, aliphatic hydrocarbons having from 1–4 carbon atoms, hydroxyl, carboxyl, amino, nitro, or thio groups. The improved catalysts of the present invention are especially useful in the hydroxylation of benzene and benzene derivatives such as chlorobenzene, fluorobenzene, toluene, ethylbenzene, and the like, into phenol or the corresponding substituted phenol. If phenol itself is the benzene derivative used as the reactant, the reaction products can include polyols such as hydroquinone, resorcinol, and catechol.

The catalysts used in the present invention are zeolites. Preferred types include ZSM-5, ZSM-11, and beta zeolite catalysts. These zeolites are commercially available from vendors such as Zeolyst International, UOP, Mobil, Degussa, and others.

If the catalyst is to be hydrothermally treated, the hydrothermal treatment can be performed by contacting the catalyst with a gas that contains water vapor, in an amount ranging from 1–100 mole % of the gas, at an elevated temperature in the range of approximately 350–950° C. The gas can of course include gases other than the water vapor. For example, it can include an inert gas such as nitrogen. The duration of the hydrothermal treatment of the catalyst preferably ranges from approximately 0.25 hours to approximately 8 hours. Additional details regarding hydrothermal treatment are given in PCT application WO 95/27560, which is incorporated here by reference.

The aqueous solution containing ferric or ferrous ions can be made with any ferric or ferrous compound that will dissociate in aqueous solution. Examples of suitable compounds include ferric nitrate, ferric ammonium oxalate, ferric chloride, and ferrous sulfate. The solution preferably has a concentration of ferric ions between approximately 0.1M and 1M. After treatment with the Fe solution, the catalyst should be calcined, e.g. at 650° C., before further processing.

The solution containing dithionate ions can be made with any dithionate compound that will dissociate in aqueous solution. A suitable example is sodium dithionate. This solution preferably has a concentration of dithionate ions between about $1\times10^{-3}$M and about 0.1M.

In the embodiment of the invention in which the catalyst is treated with acid, the acids that are preferred are mineral acids and small chelating acids that can enter the cavities in the zeolite. Nitric acid is an example of a suitable acid. The concentration of acid used in the treatment of the catalyst preferably ranges from 0.1M–4M. The acid treatment is preferably performed at a temperature between approximately room temperature (e.g., 20° C.) and approximately 100° C., for a time ranging from approximately 0.25–8 hours.

After the catalyst has been prepared, the oxidative hydroxylation is preferably performed by passing a feed gas mixture of the benzene or benzene derivative, nitrous oxide, and optionally a diluent gas such as nitrogen, argon, carbon dioxide or the like, to a bed of the zeolite catalyst at a temperature in the range of approximately 300–600° C. The residence time in the catalyst bed is preferably between about 0.25–4 sec. The feed composition and process conditions can be varied by those skilled in the art to maximize the desired product.

The present invention can be further understood from the following examples.

CBV 5020 H-ZSM 5, a zeolite catalyst, was obtained from Zeolyst International and was analyzed by XRF. (Si/Al=27.6; Fe=300 ppm.)

Catalyst sample A was prepared by hydrothermal treatment of 5020 powder at 650° C. for one hour (50% water vapor in the gas phase), followed by treatment with an aqueous solution of ferric nitrate (0.25M), and then by washing with water. A silica binder was then added and calcination was performed at 650° C. for three hours. (Si/Al=45.6; Fe=3600 ppm.)

Catalyst sample B was prepared by hydrothermal treatment of 5020 powder, followed by heating in an aqueous solution of ferric ammonium oxalate (0.25M) to 70° C. for one hour, followed by water washing and calcination at 650° C. for three hours. This was added to a silica binder and calcined to 650° C. for three hours. (Si/Al=37.8; Fe=3400 ppm.)

Catalyst sample C was prepared by hydrothermal treatment of 5020 powder followed by heating in an aqueous solution of ferric ammonium oxalate (0.25M) to 70° C. for one hour, water washing, and calcination at 650° C. for three hours. This was then treated 2× with an aqueous NaCl solution of $Na_2S_2O_4$ (sodium dithionate, $1\times10^{-2}$M) for 15 minutes at 70° C. followed by water washing, ammonium oxalate treatment (0.25M) at 70° C., water washing, and calcination at 650° C. for three hours. A silica sol binder was added and the catalyst was calcined at 650° C. for three hours. (Si/Al=41.5; Fe=300 ppm.)

Catalyst sample D was prepared by hydrothermal treatment of 5020 powder followed by heating in an aqueous solution of ferric nitrate (0.25M) to 70° C. for one hour, water washing, and calcination at 650° C. for three hours. This was then treated 3× with an aqueous NaCl solution of $Na_2S_2O_4$ (0.01M) for 15 minutes at 70° C. followed by water washing, ammonium nitrate/nitric acid treatment (0.25M $NH_4NO_3$, 0.25M $HNO_3$) at 70° C., water washing, and calcination at 650° C. for three hours. A silica sol binder was added and the catalyst was calcined again at 650° C. for three hours. (Si/Al=50.8; Fe=700 ppm.)

The catalysts prepared as indicated above were used to convert benzene to phenol. Performance parameters are summarized in the following table.

| Catalyst | A | B | C | D |
| --- | --- | --- | --- | --- |
| iron (ppm-XRF) | 300 | 3400 | 300 | 700 |
| bed temp (° C.) | 482 | 450 | 445 | 428 |
| % $C_6H_6$ | 60 | 65.18 | 61.7 | 63.96 |
| % $N_2O$ | 4.11 | 4.42 | 4.26 | 4.15 |
| Reaction time (hr) | 24.1 | 24.1 | 24.1 | 24.1 |
| avg mmol phenol/g cat | 5.55 | 4.24 | 6.33 | 6.79 |
| % Phenol ($C_6H_6$) | 96 | 94.6 | 97.2 | 97.0 |
| % Phenol ($N_2O$) | 73.5 | 48.3 | 80.9 | 85.2 |
| % $N_2O$ conversion | 61.3 | 49.3 | 65.4 | 69.4 |
| % $N_2O$ yield | 45 | 23.8 | 52.9 | 59.1 |
| % $C_6H_6$ to diols + DPO | 2.4 | 2.5 | 1.9 | 2.3 |
| % $C_6H_6$ to CO + $CO_2$ | 0.5 | 1.2 | 0.3 | 0.2 |
| meq coke/g catalyst | 1.47 | 1.8 | 1.01 | 0.77 |
| % $C_6H_6$ to coke | 1.0 | 1.7 | 0.6 | 0.5 |

(DPO = diphenyloxide)

FIG. 1 shows the change over time of the percentage of phenol in the product stream when catalyst samples A (referred to as "Phenol-steam" in the legend of the figure) and B ("Phenol-Fe") were used. The introduction of iron created more active sites (as evidenced by a reduction in bed temperature required for conversion of nitrous oxide), however poorer selectivity resulted along with poorer catalyst stability. This may have been due to the introduction of iron oxides which promote over-oxidation pathways.

Figure 2:
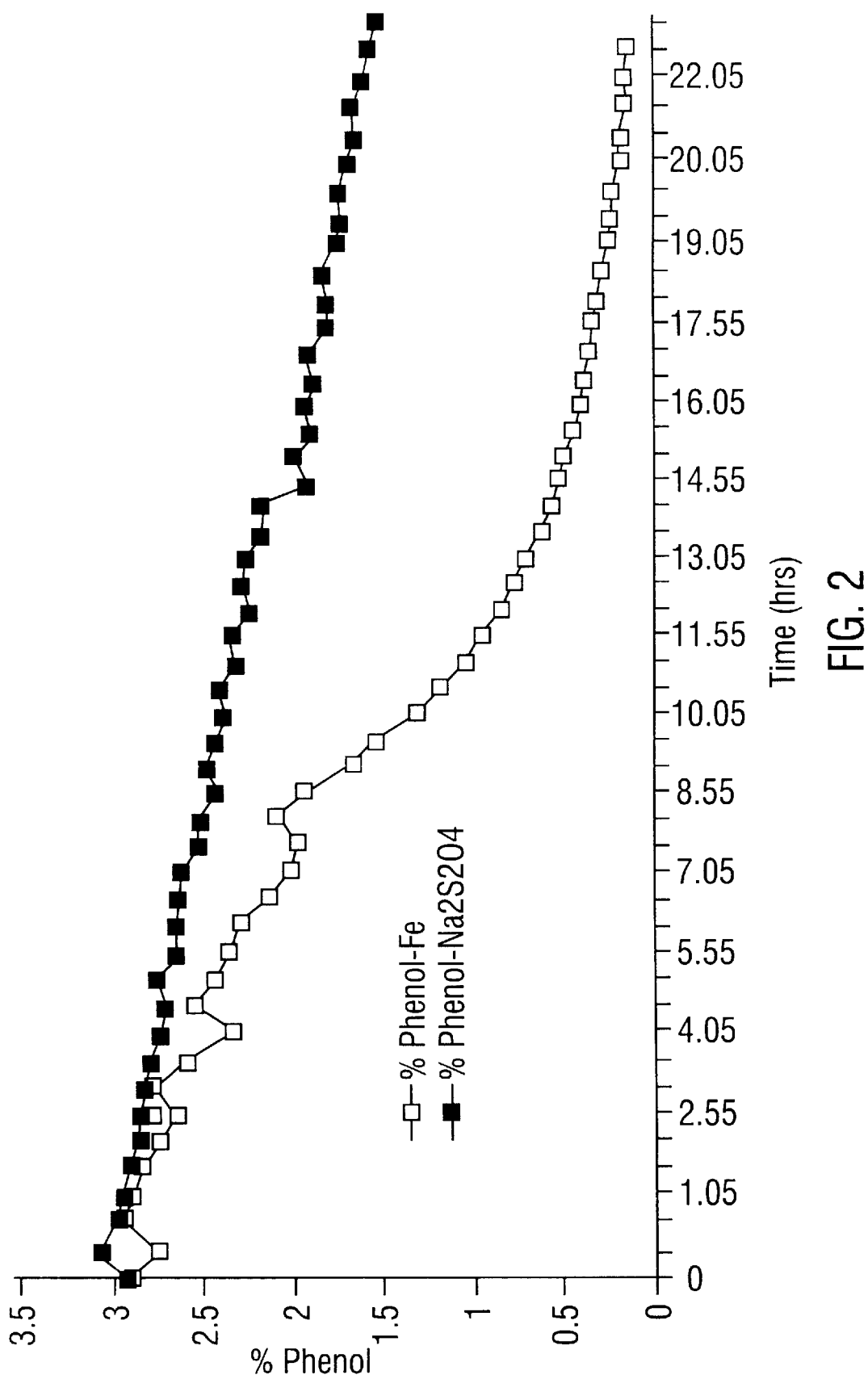
FIG. 2 is a similar graph for a benzene hydroxylation process in which (a) the catalyst had been hydrothermally treated and then had iron added by treatment with ferric ammonium oxalate ("Phenol-Fe"), or (b) the catalyst had been hydrothermally treated and then had iron added by treatment with ferric ammonium oxalate followed by dithionate treatment ("Phenol-$Na_2S_2O_4$").

FIG. 2 compares the results for phenol production using the catalyst sample B ("Phenol-Fe") or the catalyst sample C ("Phenol-$Na_2S_2O_4$"). The dithionate treatment greatly increased catalyst selectivity and stability without loss of activity.

Catalyst sample E was prepared by treatment of 5020 powder (from Zeolyst International) with an aqueous solution of ferric nitrate (0.25M) at 70° C. for 1 hr after which time the treated zeolite was collected by filtration and washed with water. The solid was calcined at 650° C. followed by hydrothermal treatment at 650° C. for 1 hr using an atmosphere containing 50% water vapor. The resulting material was treated with an aqueous solution of sodium dithionate (0.01M) at 70° C. for 15 min. The zeolite was collected by filtration and washed with water. This was then treated with 0.25M nitric acid/0.25M ammonium nitrate at 70° C. for 1 hr with the resulting material collected by filtration, washed with water and then calcined at 650° C. The catalyst was bound to silica using a silica sol solution prior to use.

The catalyst was used to convert benzene to phenol. Performance parameters are summarized in the following table.

| Catalyst | E |
| --- | --- |
| % benzene | 63 |
| % nitrous oxide | 4.15 |
| bed temp ° C. | 418 |
| rxn time (hr) | 21.6 |
| avg mmol phenol/g cat | 6.72 |
| avg % benzene selectivity | 97.1 |
| avg % nitrous oxide selectivity | 84.3 |
| % benzene conversion | 4.17 |
| % nitrous oxide conversion | 73.2 |
| % diols + DPO | 2.1 |
| % CO + $CO_2$ | 0.3 |
| % coke | 0.5 |

Figure 3:
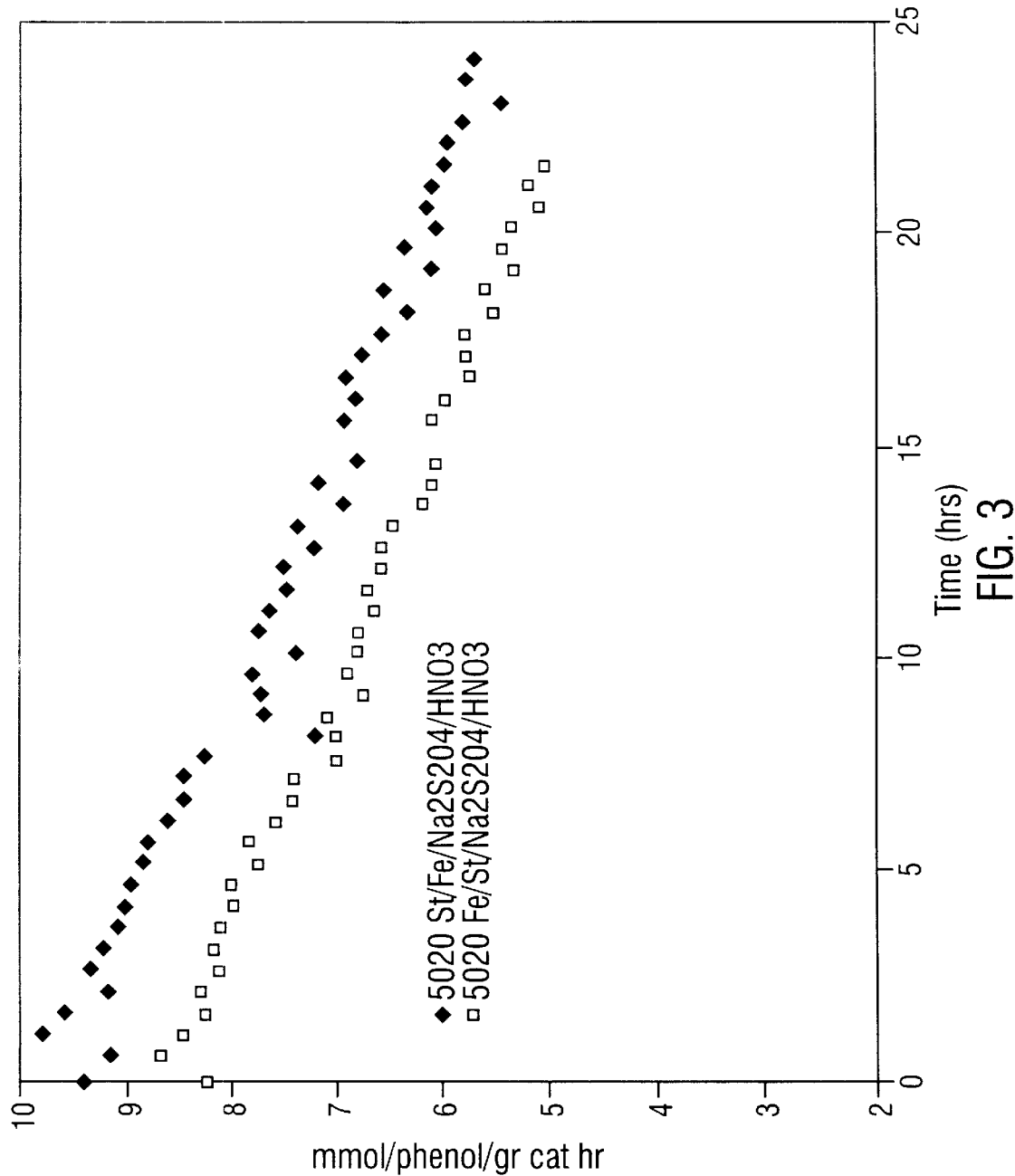
FIG. 3 is a graph of the change over time in the productivity of catalyst in converting benzene to phenol, where the catalyst had been (a) hydrothermally treated, then treated with a solution containing ferric ions, then treated with a solution containing dithionate ions, and then treated with acid ("5020-St/Fe/Na2S2O4/HNO3"), or (b) treated with a solution containing ferric ions, then hydrothermally treated, then treated with a solution containing dithionate ions, and then treated with acid ("5020-Fe/St/Na2S2O4/HNO3").

FIG. 3 shows the productivity (in mmol phenol/g cat/hr) in converting benzene to phenol of two catalyst samples. The legend 5020-St/Fe/Na2S2O4/HNO3 represents catalyst sample D. The legend 5020-Fe/St/Na2S2O4/HNO3 represents catalyst sample E. Sample E, as described above, was treated with a solution of ferric ions, then hydrothermally treated, and subsequently treated with a solution of dithionate ions and then a nitric acid solution. In contrast, sample D was hydrothermally treated, and then sequentially treated with a solution of ferric ions, a solution of dithionate ions, and a solution of nitric acid. FIG. 3 shows that acceptable catalyst productivity can be obtained whether the hydrothermal treatment precedes the treatment with a solution of ferric ions or vice versa.

Figure 4:
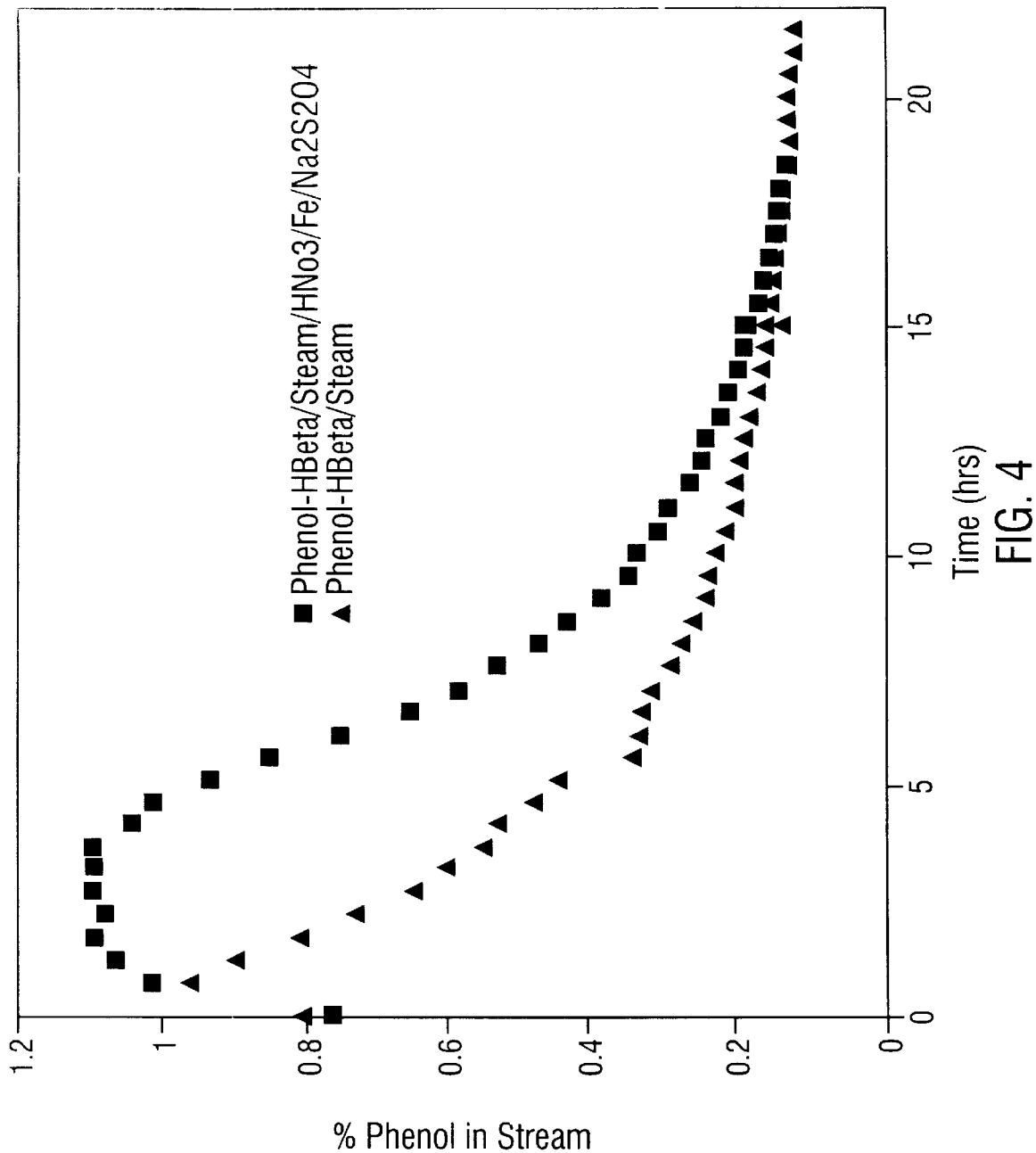
FIG. 4 is a graph of the change over time in the percentage of phenol in the product stream of a benzene hydroxylation process using catalyst in which (a) the catalyst had been hydrothermally treated, then treated with acid, then treated with a solution containing ferric ions, and then treated with a solution containing dithionate ions ("Phenol-HBeta/Steam/HNO3/Fe/Na2S2O4"), or (b) hydrothermally treated, but not treated with solutions of ferric ions or dithionate ions ("Phenol-HBeta steam").

FIG. 4 shows phenol production for two H-Beta zeolite catalysts, one hydrothermally treated and then treated with nitric acid and solutions of ferric ions and dithionate ions, the other only hydrothermally treated. Conditions for the hydrothermal treatment, acid, ferric and dithionate treatments were similar to those described above for the H-ZSM 5 catalysts. The catalyst treated with ferric ions and dithionate ions exhibited greater activity and on-stream time than the catalyst that was only hydrothermally treated.

The above results show that a method has been developed for the selective introduction of active sites into a zeolite catalyst for hydroxylation of benzene or a derivative thereof. The treatment does not adversely affect selectivity and stability of the catalyst, and permits the conversion of benzene to phenol at a temperature approximately 50° C. lower than would otherwise be required.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A method of preparing a catalyst for the oxidation of an aromatic compound, comprising treating a zeolite catalyst with an aqueous solution containing ferric or ferrous ions, and treating the catalyst with an aqueous solution containing dithionate ions.

2. The method of claim 1, where the aqueous solution contains ferric ions and is selected from the group consisting of aqueous solutions of ferric nitrate, ferric ammonium oxalate, and ferric chloride.

3. The method of claim 1, further comprising the step of treating the catalyst with an acid.

4. The method of claim 1, further comprising the step of hydrothermally treating the catalyst.

5. The method of claim 4, where the hydrothermal treatment of the catalyst comprises exposing the catalyst to a gas comprising 1–100 mole percent water at a temperature between approximately 350–950° C.

6. The method of claim 4, where the hydrothermal treatment is subsequent to the treatment with the solution containing ferric or ferrous ions.

7. The method of claim 4, where the treatment with the solution containing ferric or ferrous ions is subsequent to the hydrothermal treatment.

8. A method of preparing a catalyst for oxidation of benzene or a derivative thereof, comprising (a) hydrothermally treating a zeolite catalyst by exposing the catalyst to a gas comprising 1–100 mole percent water at a temperature between approximately 350–950° C., (b) treating the catalyst with an aqueous solution containing ferric or ferrous ions, (c) treating the catalyst with an aqueous solution containing dithionate ions, and (d) treating the catalyst with an acid.

9. A method of preparing a catalyst for oxidation of benzene or a derivative thereof, comprising (a) hydrothermally treating a zeolite catalyst by exposing the catalyst to a gas comprising 1–100 mole percent water at a temperature between approximately 350–950° C., (b) treating the catalyst with an aqueous solution containing ferric or ferrous ions, (c) calcining the catalyst, (d) treating the catalyst with an aqueous solution containing dithionate ions, (e) treating the catalyst with an acid, and (f) calcining the catalyst.

* * * * *